(12) United States Patent
Fomitchov et al.

(10) Patent No.: US 7,567,346 B2
(45) Date of Patent: Jul. 28, 2009

(54) SYSTEM AND METHOD FOR MULTIMODE IMAGING

(75) Inventors: Pavel A. Fomitchov, New York, NY (US); Eugene Barash, Niskayuna, NY (US); Ahmad Yetka, Somerset, NJ (US); Joseph Masino, III, Howell, NJ (US)

(73) Assignee: General Electric Company, Schenectady, NY (US)

( * ) Notice: Subject to any disclaimer, the term of this patent is extended or adjusted under 35 U.S.C. 154(b) by 44 days.

(21) Appl. No.: 11/363,938

(22) Filed: Mar. 1, 2006

(65) Prior Publication Data

US 2007/0206192 A1 Sep. 6, 2007

(51) Int. Cl.
*G01N 21/25* (2006.01)
(52) U.S. Cl. .................. 356/416; 382/282; 382/284; 359/385; 359/368
(58) Field of Classification Search .......... 356/300, 356/305, 309, 310, 317, 318, 319, 416; 359/196, 359/385, 368; 382/282, 284, 291, 294, 298, 382/100, 128, 173
See application file for complete search history.

(56) References Cited

U.S. PATENT DOCUMENTS

| | | | |
|---|---|---|---|
| 4,826,299 A | | 5/1989 | Powell |
| 6,388,788 B1 * | | 5/2002 | Harris et al. ............. 359/196 |
| 6,677,565 B1 | | 1/2004 | Wahl et al. |
| 6,687,419 B1 * | | 2/2004 | Atkin ...................... 382/284 |
| 2005/0271274 A1 * | | 12/2005 | Urano et al. ............. 382/173 |
| 2006/0012871 A1 * | | 1/2006 | Funk et al. .............. 359/385 |

FOREIGN PATENT DOCUMENTS

WO WO 95/11461 4/1995

OTHER PUBLICATIONS

Hooper et al., "Developments and Applications of Photon Imaging for Biomolecular Screening," The Society for Biomolecular Screening (1995).
Flushberg et al., "Fiber-optic fluorescence imaging," Nature Methods 2:12, 941-50 (Dec. 2005).
Helmchen, "Miniaturization of fluorescence microscopes using fibre optics," Exp. Physiol 87:6, 737-45 (2002).
Product Specification (No. DTS0105) by OZ Optics Limited, "RGB (Red/Green/Blue) Combiner and Delivery Systems," pp. 1-7 (Jun. 10, 2005).

* cited by examiner

*Primary Examiner*—Kara E Geisel
*Assistant Examiner*—Abdullahi Nur
(74) *Attorney, Agent, or Firm*—Yonggang Ji

(57) ABSTRACT

A system and method for multimode imaging of at least one sample is disclosed. The system includes at least one light source; an optical system selected responsive to a mode of operation of the imaging system; and a detector capable of selective reading of pixels. The at least one sample is moved relative to the optical system using a sample movement technique selected from the group consisting of step sample moving and continuous sample moving. The method includes the steps of (1) selecting a mode of operation for the imaging system; (2) transmitting light from at least one light source through an optical system selected in response to the mode of operation for the imaging system; (3) moving the at least one sample relative to the optical system using a sample movement technique selected from the group consisting of step sample moving and continuous sample moving; and (4) selectively reading pixels with a detector.

29 Claims, 10 Drawing Sheets

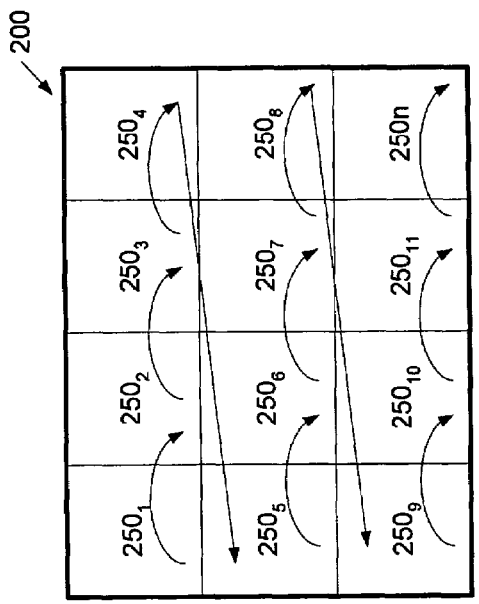
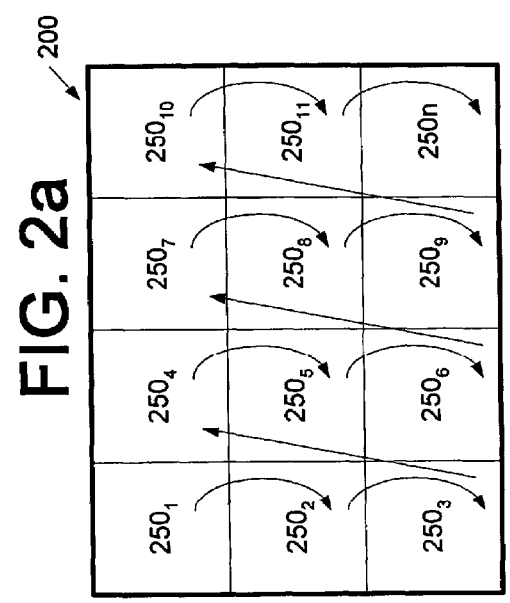
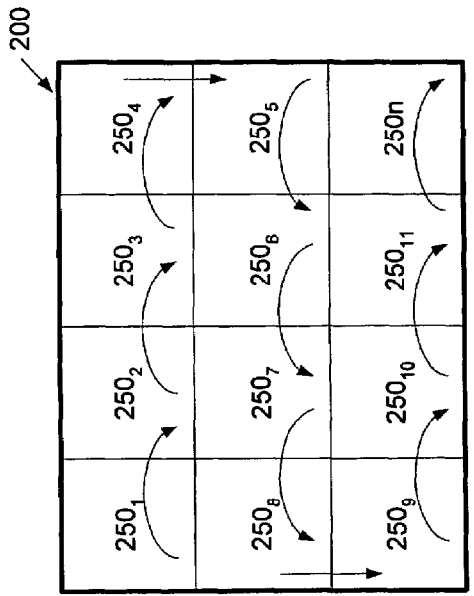
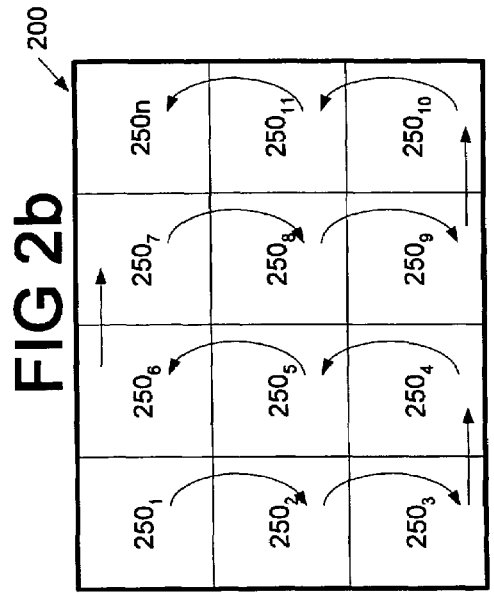
FIG. 2a
FIG. 2b
FIG. 2c
FIG. 2d

Alignment Techniques

| Optical Method | a) Edge Detection | b) Reflected light contrast | c) Diffraction (Fresnel zone target) | d) Fluorescence |
|---|---|---|---|---|
| Alignment Signal | | | | |
| Wavelength | HeNe laser (633nm) | Blue (436nm) Green (547nm) or Yellow (578nm) | HeNe laser (633nm) | Cy3 (532nm) Cy5 (633nm) Cy7 (690nm) |

FIG. 10

SYSTEM AND METHOD FOR MULTIMODE IMAGING

BACKGROUND OF THE INVENTION

1. Field of the Invention

The present invention generally relates to imaging systems, and, more particularly, to a system and method for multimode imaging.

2. Description of the Related Art

Numerous optical imaging system designs have been developed, each with its own imaging techniques. In the context of microscopy, wide field imaging techniques have been employed in certain systems, while confocal imaging techniques have been used in other systems.

Wide-field imaging involves illuminating a sample and detecting the image of substantially the entire field of view. Wide-field imaging has been used for numerous applications. Fluorescence microscopy is an example of one application that has utilized wide field imaging.

Confocal imaging utilizes a specialized illumination and detection arrangement that images only a selected portion of the imaging system's field of view. In addition to conventional imaging optics, confocal imaging includes a detector having a field of view, an aperture that defines a subset of a field of view, and an illumination system that illuminates an area of sample that is optically conjugated to the field of view. Confocal imaging is capable of providing better axial resolution than wide field imaging by rejecting out of focus light and enabling optical sectioning. In the context of fluorescence microscopy, confocal imaging improves the signal to noise ratio by rejection of background fluorescence that may come from supporting medium, or outside the subset of the imaging area.

SUMMARY OF THE INVENTION

A system and method for multimode imaging of at least one sample is disclosed. According to one embodiment of the invention, the system includes at least one light source; an optical system selected responsive to a mode of operation of the imaging system; and a detector capable of selective reading of pixels. The at least one sample is moved relative to the optical system using a sample movement technique selected from the group consisting of step sample moving and continuous sample moving.

According to another embodiment of the present invention, a method for multimode imaging of at least one sample is disclosed. The method includes the steps of (1) selecting a mode of operation for the imaging system; (2) transmitting light from at least one light source through an optical system selected in response to the mode of operation for the imaging system; (3) moving the at least one sample relative to the optical system using a sample movement technique selected from the group consisting of step sample moving and continuous sample moving; and (4) selectively reading pixels with a detector.

The mode of operation may be wide field mode, fixed line confocal mode, scanning line confocal mode, point confocal mode, or through transmission mode.

The optical system may include a beam forming element that is selected in response to the mode of operation for the imaging system, a beam deflecting device that deflects the light on the sample, and a beam collimator that collimates the light. The beam forming element may include Powell lenses, cylindrical lenses, diffraction gratings, holographic elements, focusing mirrors, conventional lenses having spherical surfaces, conventional lenses having aspherical surfaces, and combinations thereof. The beam collimator may be a lens-based collimator and a mirror-based collimator. The beam deflecting device may include a scanning mirror and at least one actuator. The system may further include at least one optical filter.

It is a technical advantage of the present invention that a system and method for multimode imaging is disclosed. It is another technical advantage of the present invention that the system may operate in wide field mode, fixed line confocal mode, scanning line confocal mode, point confocal mode, or through transmission mode. It is still another technical advantage of the present invention that the step sample moving and continuous sample moving are used to move the sample.

BRIEF DESCRIPTION OF THE DRAWINGS

For a more complete understanding of the present invention, the objects and advantages thereof, reference is now made to the following descriptions taken in connection with the accompanying drawings in which:

FIGS. 2a-2d are schematics of step sample moving techniques according to embodiments of the present invention;

FIG. 10 are illustrations of registration techniques using alignment marks according to embodiments of the present invention.

DETAILED DESCRIPTION OF PREFERRED EMBODIMENTS

Figure 1:
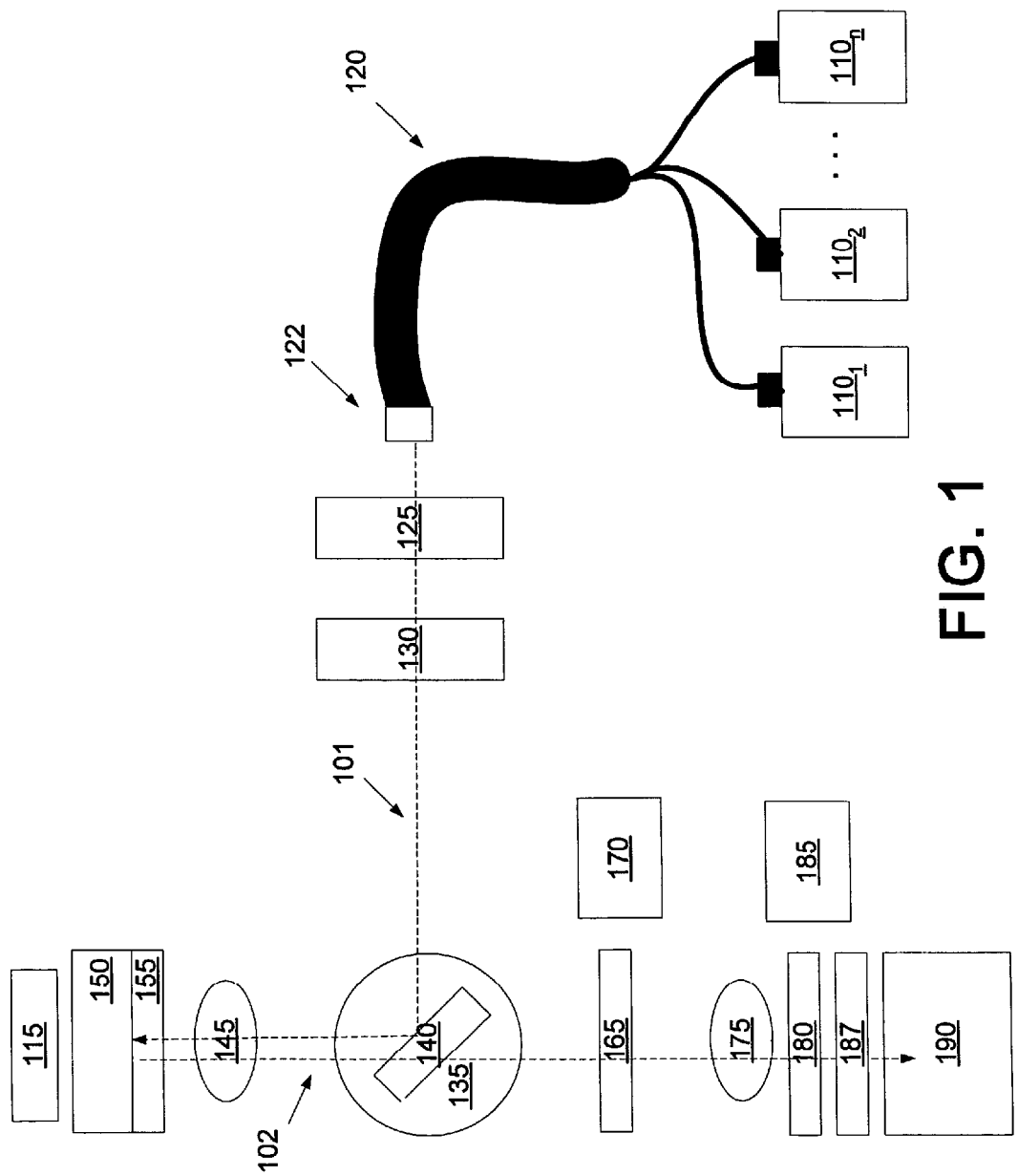
FIG. 1 is a block diagram of a system for multimode imaging according to one embodiment of the present invention.

The system and method of the present invention are suitable for use with wide field, true (point) confocal, and line confocal microscopes Examples of such devices are disclosed in U.S. patent application Ser. No. 11/184,444 entitled "Method and Apparatus for Fluorescent Confocal Microscopy"; U.S. patent application Ser. No. 11/320,676 entitled "Autofocus Method And System For An Automated Microscope"; and U.S. patent application Ser. No. 11/320,675 entitled "System And Method For Fiber Optic Bundle-Based Illumination For Imaging System." The disclosures of these documents are hereby specifically incorporated by reference in its entirety.

Preferred embodiments of the present invention and their advantages may be understood by referring to FIGS. 1-10, wherein like reference numerals refer to like elements.

Referring to FIG. 1, a system for multimode imaging according to one embodiment of the present invention is schematically presented and includes one or more light sources $110_1$-$110_n$ to excite fluorescent (or fluorescently stained or labeled) target 150 and one or more detectors 190 to detect fluorescent emissions. System 100 may contain other components as would ordinarily be found in confocal and wide field fluorescent microscopes. The following sections describe these and other components in more detail. For a number of the components there are multiple potential embodiments.

For illustration only, excitation light is illustrated as dashed line 101, while reflected light is illustrated as dashed line 102.

Light sources $110_1$-$110_n$ may include any source capable of delivering light of the excitation wavelength to the target. Examples of suitable light sources include lasers, laser diodes, light emitting diodes, and lamps. Other light sources may be used as appropriate.

In one embodiment, two or more lasers covering the optical spectrum from the near IR to the near UV are provided as light sources $110_1$-$110_4$. Any practical number of lasers can be used, and the number of light sources provided may depend on the number of fluorescent dyes present in the sample that require different excitation light wavelengths.

As disclosed in U.S. patent application Ser. No. 11/184,444, light from the light sources is coupled to the rest of the system by either delivering the light as a free space beam of the appropriate spatial and temporal parameters, such as diameter, direction and degree of collimation or, as disclosed in U.S. patent application Ser. No. 11/320,675, via fiber optic light delivery system. In the free space embodiment (not shown), a laser selection module is used to select the laser to be transmitted through free space. In the fiber optic light delivery embodiment, shown in FIG. 1, light from light sources $110_1$-$110_n$ is delivered through fiber optic bundle 120 or via a fiber optic beam combiner.

In one embodiment, light source 115 may be provided behind sample 150. This allows system 100 to operate in through transmission mode. Light source may be any suitable light source, including lasers, laser diodes, light emitting diodes, lamps, and combinations thereof. Other light sources may be used as appropriate.

Light exiting either fiber optic bundle 120 or free space may be provided to beam collimator 125. Beam collimator 125 may be a lens-based collimator or a mirror-based collimator. Beam collimator 125 converts a diverging beam into a collimated beam. Alternately, beam collimator 125 may be used as a beam expander.

The excitation light may pass through beam forming element 130. Beam forming element 130 allows system 100 to operate in line confocal mode, point confocal mode, or in wide field mode. Beam forming element 130 may perform a beam collimator/expander function.

In one embodiment, if system 100 is operated in line confocal mode, beam forming element 130 may convert the collimated beam of laser light into a focused beam diverging in one direction only. The full divergence angle of the output beams Dq may calculated by the following equation:

$$Dq = 2 * \arctan(D/(2*f))$$

where f is the focal length of microscope objective 145, and D is the linear dimension of the imaging area on target 150 along the axis of the line. In one embodiment, a Powell lens, such as that disclosed in U.S. Pat. No. 4,826,299, the disclosure of which is incorporated by reference in its entirety, may be used. In another embodiment, a cylindrical lens may be used.

Other suitable beam forming elements 130 include focusing mirrors, diffraction gratings and holographic elements.

In another embodiment, if system 100 is to be operated in wide field mode, beam forming element 130 may be a conventional lens with spherical or aspherical surfaces. In another embodiment, beam forming element 130 may be a focusing mirror. The necessary beam forming element 130 may be automatically moved into position once a corresponding mode of operation is selected.

Following beam forming element 130, light is directed by beam deflecting device 140, such as a scanning mirror. Beam deflecting device 140 is used to adjust a position of the illumination area, such as line, point, or wide field on sample 150.

In one embodiment, beam deflecting device 140 may include a narrow mirror centered on, or axially offset from, the rear of microscope objective 145. This embodiment has a geometry and reflective property as follows:

Width ~1/10 times the diameter of the rear aperture of the objective;
Length ~1.6 times the diameter of the rear aperture of the objective;
Optically flat; and
Highly reflective 300 nm to 800 nm.

These particular properties of the mirror provide several key advantages. First, it makes it possible to use a single mirror for all excitation wavelengths. Relative to a multiband dichroic mirror this greatly increases the flexibility in adapting the system to a wide range of light sources.

Second, it uses the rear aperture of the objective at its widest point. This leads to the lowest achievable level of diffraction which in turn yields the narrowest achievable width of the line of laser illumination at the sample.

Third, the field of view that can be achieved is large as is possible with the simple one-tilting-mirror strategy. By using two mirrors, or using a single mirror having two axes of rotation, one can simultaneously change the direction of the beam and translate the beam.

Beam deflecting device 140 may also be a dichroic mirror. The design of the dichroic mirror will be such that the radiation from all excitation lasers is efficiently reflected, and that light in the wavelength range corresponding to fluorescence emission is efficiently transmitted. An example of a suitable dichroic mirror is a multi-band mirror based on Rugate technology.

In one embodiment, beam deflecting device 140 is selected according to the mode of operation. For example, if system 100 is operated in true (point) confocal mode, beam deflecting device 140 may be a dichroic mirror that may be scanned in two directions. In another embodiment, if system 100 is operated in wide field mode or in line confocal mode, beam deflecting device may be a narrow mirror that may be fixed or scanned in one direction. The necessary beam deflecting device 140 may be automatically or manually moved into position once a corresponding mode of operation is selected.

Beam deflecting device 140 may be scanned in one or two directions by actuator 135. In one embodiment, actuator 135 may be a galvanometer with an integral sensor for detecting the angular position. The galvanometer is driven by a suitably-tuned servo system. The bearing system is based on flexures to effectively eliminate wear and issues with friction in the bearing. An example of a galvanometer is the Cross Flexure Pivot Suspension Moving Magnet Galvanometer, available from Nutfield Technology, Inc., 49 Range Road, Windham, N.H. 03087-2019.

In one embodiment, when system 100 is operated in line confocal mode, actuator 135 moves beam deflecting device 140 to cause excitation light to move across sample 150.

In another embodiment, when system 100 is operated in true (point) confocal mode, actuator 135 moves beam deflecting device 140 in two directions to cause light 120 to move across sample 150.

In yet another embodiment, when system 100 is operated in wide field mode, actuator 135 may fix beam deflecting device 140 relative to sample 150. This may be at, for example, a 45 degree angle with respect to the axis of illumination. In still another embodiment, when system 100 is operated in wide field mode, actuator 135 may move beam deflecting device 140 relative to sample 150 at a frequency that is greater than the frequency at which detector 190 acquires light. Such movement may provide a more uniform light field over sample 150.

Detector 190 is provided for detecting fluorescence from sample 150. In one embodiment, detector 190 may include CMOS and CCD detectors that are capable of detecting the fluorescent light and generating an image. Detector 190 may be capable of an independent reset and readout of pixels (random access feature).

In one embodiment, multiple detectors may be provided, as discussed in U.S. patent application Ser. No. 11/184,444.

Optical filter 180 may be provided to transmits the reflected light attenuate the light at other wavelengths. In one embodiment, optical filter 180 may be a linear variable filter (e.g., Schott Veril filter). In another embodiment, standard, dye-specific fluorescence filters may be used. In yet another embodiment, band pass filters for providing multispectral imaging may be used. In another embodiment, no filter may be used.

In one embodiment, additional aperture 187 may be provided in front of detector 190. In one embodiment, additional aperture 187 is used when system 100 operates in line confocal mode. Additional aperture 187 may be a physical slit in a nontransparent material, such as steel, aluminum, ceramics, etc.

In such an embodiment, the width of physical slit may be narrower than the pixel width of the pixels in detector 190. This provides an increase in the degree of confocality of system 100. In one embodiment, the width of the physical slit in additional aperture 187 may be adjustable. This allows the width of the physical slit may be adjusted to provide widths at other than pixel widths. For example, the width of the physical slit may be one and one-half pixel widths.

The insertion and removal of additional aperture 187 may be automatic or it may be manual. Similarly, the adjustment of the width of the physical slit may be automatic or it may be manual.

In one embodiment, if the physical limitations of detector 190 do not allow placement of additional aperture 187 directly above the pixels in detector 190, an additional optical system (not shown) may be located between additional aperture 187 and detector 190 to re-image the physical slit on detector 190. For example, the additional optical system can be a relay lens.

The remainder of system 100, including microscope objective 145, sample support 155, optical filter 165, actuator 170 for optical filter 165, image forming lens 175, and actuator 185 for optical filter 180, is fully described in U.S. patent application Ser. No. 11/184,444.

Although the system and method of the present invention is described in the context of the system of FIG. 1, it should be recognized that the present invention is not limited to such a system. Similarly, although the system and method of the present invention is described in the context of a fluorescent system, it should be recognized that the system and method of the present invention may be used in a non-fluorescent system.

As discussed above, the system of the present invention may operate in wide field, true (point) confocal, and line confocal modes. Line confocal mode includes both fixed line confocal mode and scanning line confocal mode. In fixed line confocal mode, beam deflecting device 140 is fixed thereby fixing the position of the illumination line over sample 150. In scanning line confocal mode, beam deflecting device 140 scans the illumination line over sample 150.

To image a sample, the system of the present invention may use a variety of techniques to adjust the relative position of the sample and the illumination system relative to each other. Such techniques will be discussed below.

In one embodiment, the relative position between the illumination system and the sample may be adjusted by moving the sample. This may be accomplished by moving the sample support, on which sample is provided. An example of a system to accomplish this is disclosed in U.S. Pat. No. 6,388,788, entitled "Method and apparatus for screening chemical compounds," the disclosure of which is incorporated by reference in its entirety.

In another embodiment, the relative position between the illumination system and the sample may be adjusted by moving the illumination system. For example, this may involve moving the entire illumination system, or it may involve moving only a portion of the illumination system. In yet another embodiment, the relative position between the illumination system and the sample may be adjusted by a combination of moving the sample and the illumination system.

Referring to FIGS. 2*a-d*, the relative position between the illumination system and the sample may be adjusted using a "step sample moving" technique. In general, in step sample moving, during image acquisition, the relative position of the sample and the illumination system remains fixed. Step sample moving can be used when the system is operated in several modes, including wide field mode and line confocal mode.

Step sample moving is used to detect a sequence of images of sample 200. In this technique, the image area of sample 200 is "broken" into a plurality of smaller image areas $250_1, \ldots 250_n$. Each image area $250_n$ is imaged separately before moving to the next image area $250_{n+1}$ to image that image area $250_{n+1}$. In one embodiment, the image areas $250_1, \ldots 250_n$ may be imaged by row. In another embodiment, the image areas $250_1, \ldots 250_n$ may be imaged by column. In yet another embodiment, the imaging may be based on the location of items of interest. For example, the movement may be random if sample 200 has many small objects, such as cells, that are randomly distributed over the slide or well.

FIGS. 2*a*-2*d* illustrate different ways of implementing the step sample moving technique. In FIG. 2*a*, sample 200 is imaged by rows using a relative movement that is similar to the movement of a typewriter (e.g., left to right, carriage return, left to right) according to one embodiment of the present invention. In FIG. 2*b*, sample 200 is imaged by rows in both directions. In FIG. 2*c*, sample 200 is imaged by columns in one direction. In FIG. 2*d*, sample 200 is imaged by columns in both directions. Other movement directions and techniques may be used as desired.

Each image area $250_n$ may be imaged so that it overlaps with its adjacent image areas.

Figure 3:
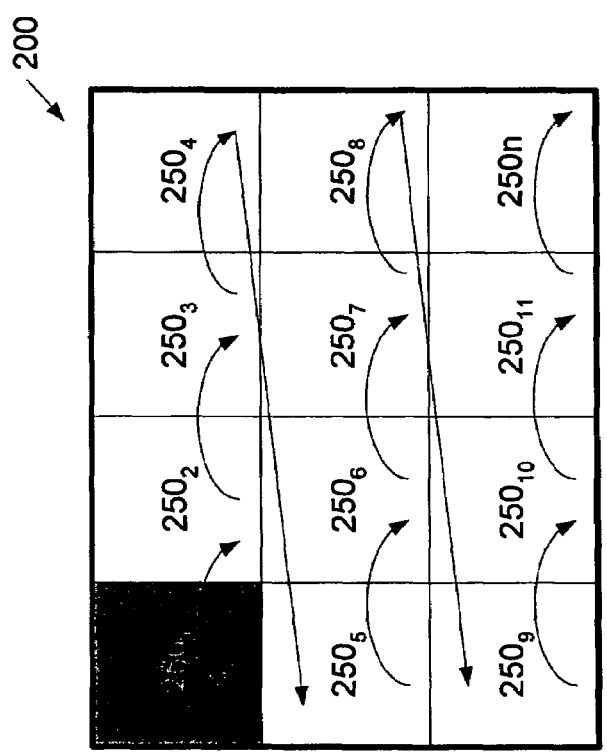
FIG. 3 is a schematic of a step sample moving technique using wide field mode according to one embodiment of the present invention.

Referring to FIG. 3, in one embodiment, the system may operate in wide field mode, and the step sample moving technique is used. In this embodiment, a wide field "snapshot" is taken of each image area $250_1$-$250_n$ separately. During each "snapshot," both sample 200 and the illumination system remain fixed relative to each other. Sample 200 is imaged as discussed above.

Figure 4:
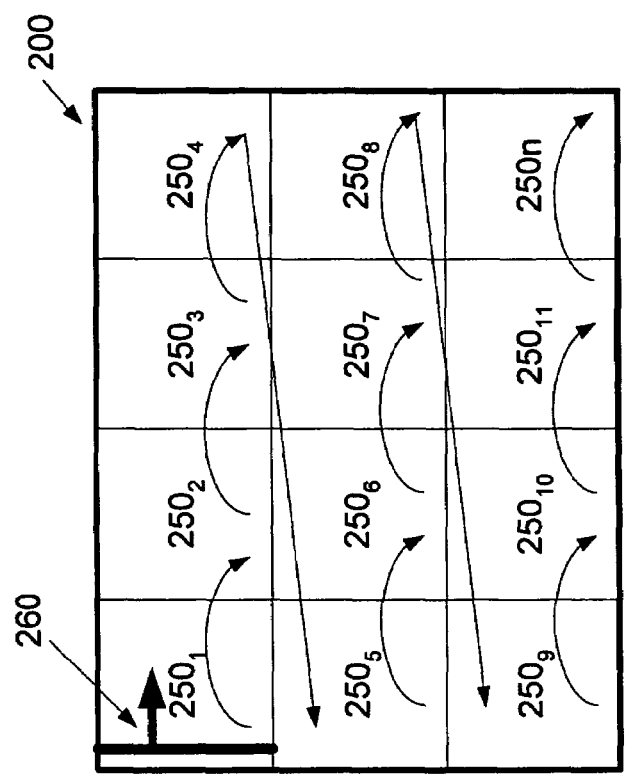
FIG. 4 is a schematic of a step sample moving technique using line confocal mode according to one embodiment of the present invention.

Referring to FIG. 4, in one embodiment, the system may operate in scanning line confocal mode, and the step sample moving technique may be used. In this embodiment, the illumination system illuminates line 260 on each image area $250_1$-$250_n$ separately. In one embodiment, during this imaging, both sample 200 and the illumination system remain fixed relative to each other. In this embodiment only the scanning portion of the illumination system moves and causes illumination line 260 to move across sample 200. Sample 200 is imaged as discussed above.

Although FIGS. 3 and 4 illustrate only one type of step sample moving technique, it should be recognized that other step sample moving techniques may be used as desired.

Figure 5A:
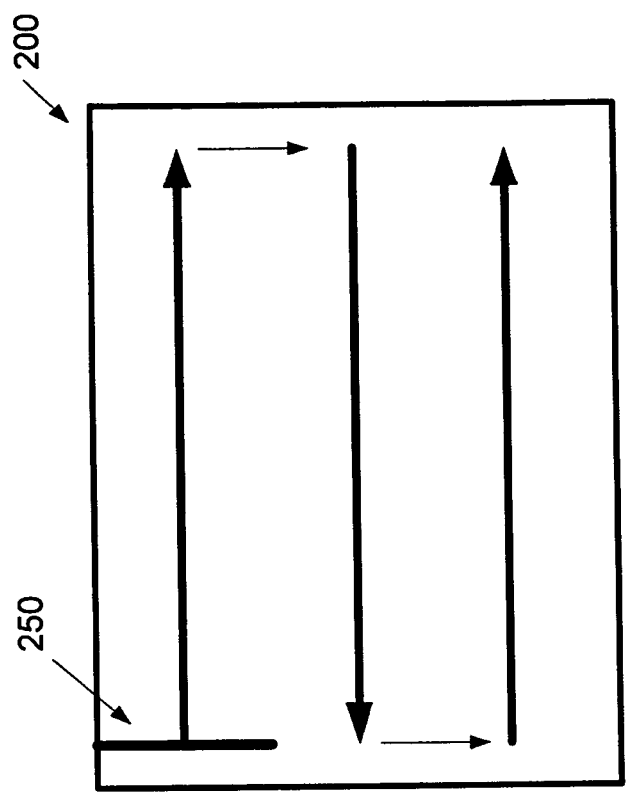
FIGS. 5a-5b are schematics of continuous sample moving techniques according to embodiments of the present.invention.
Figure 5B:
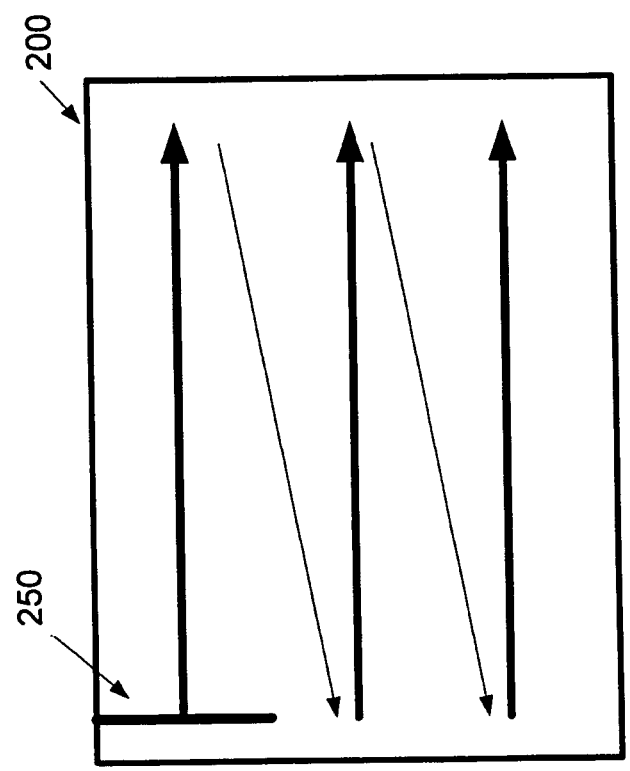

FIGS. 5a and 5b illustrate the "continuous sample moving" technique according to another embodiment of the present invention. In general, in continuous sample moving, during image acquisition, the relative position of the sample and the illumination system is adjusted, while the optics of the illumination system remain fixed. Continuous sample moving is preferably used when the system operates in fixed line confocal mode, but it may also be used when the system operates in other modes, such as wide field mode.

In one embodiment, additional aperture 187 may be employed when continuous sample moving and fixed line confocal mode are used.

Continuous sample moving in combination with fixed line confocal mode allows for an image larger than the field of view of the imaging system to be acquired in a single image. Accordingly, continuous sample moving can also be used to image more than one sample, i.e., batch sample processing, in a single image.

As shown in FIG. 5a, the system may operate in fixed line confocal mode and sample 200 is imaged in one direction by moving sample 200 relative to the illumination system in one direction. Sample 200 is returned to its initial position and the process is repeated. In another embodiment, shown in FIG. 5b, the sample may be imaged in both directions. Other movement directions and techniques may be used as desired.

Alternatively, illumination line 260 may be moved to cover another linear section of the sample as the relative position of the sample is moved back to its initial position as shown in FIG. 5a or b. In this case, the sample is imaged as it passes under the beam in both directions.

In another embodiment, the system may operate in wide field mode and continuous sample moving may be used. In this embodiment, illumination light is provided to the sample in pulses as the sample moves relative to the illumination system.

Figure 6:
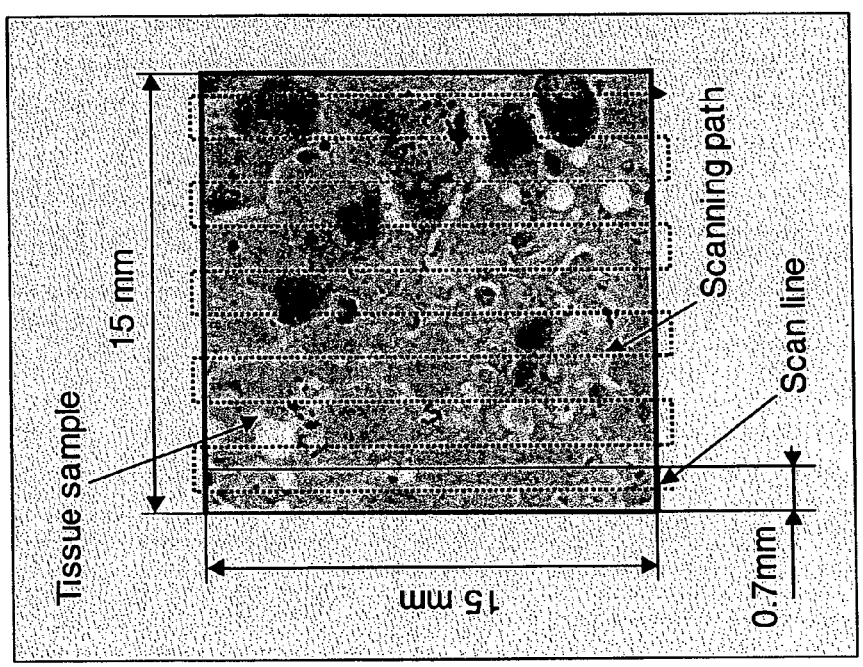
FIG. 6 is a schematic of a continuous sample moving technique using line confocal mode according to one embodiment of the present invention.

An example of the continuous sample moving technique while the system operates in fixed line confocal mode is shown in FIG. 6. In this figure, a sample having a dimension of 15×15 mm is provided on a standard microscope slide. An illumination line from the illumination system is provided, and may have a length of 0.7 mm. The magnification is 40×. The scanning speed is 100 mm/second. The detector is a fast CCD/CMOS camera.

In this embodiment, the sample must move relative to the illumination system to make 22 passes to complete the imaging of the sample. The total scan length is 330 mm. The ideal scan time is 330/100, equaling 3.3 seconds per standard microscope slide. Correction for additional delays for sample support acceleration, deceleration, sample support shift between lines, etc, is 300-400% of the ideal scan time. The realistic scan time is 15 seconds.

Figure 7:
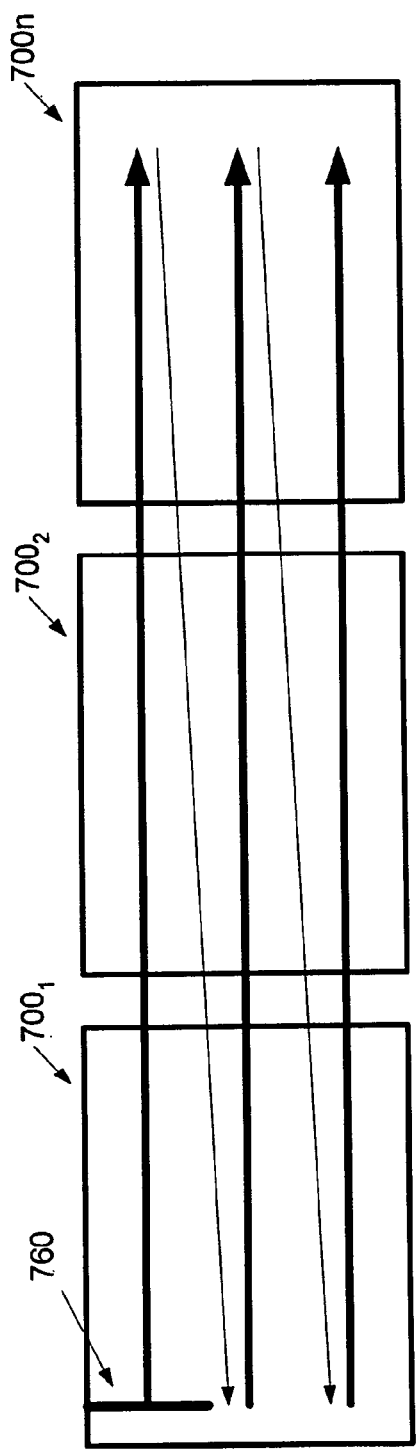
FIG. 7 is a schematic of a continuous sample moving technique using line confocal mode with multiple samples according to an embodiment of the present invention.
Figure 8:
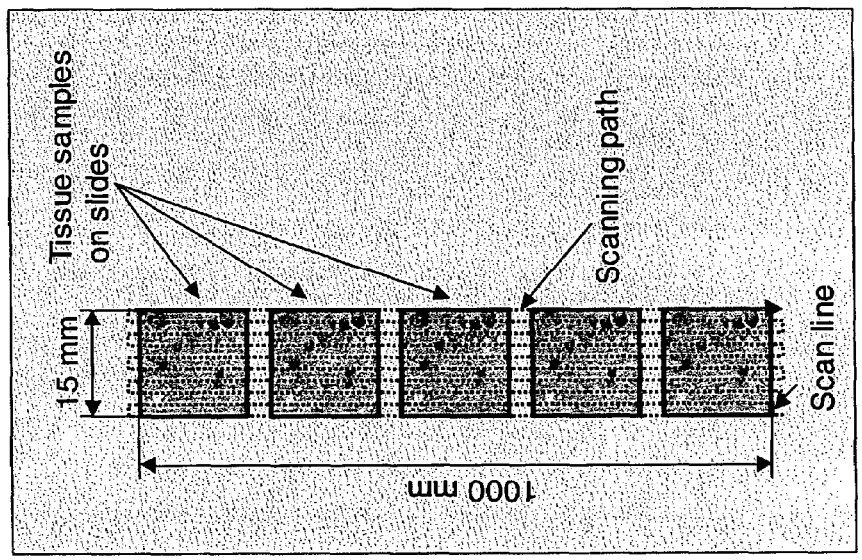
FIG. 8 is a schematic of a continuous sample moving technique using line confocal mode with multiple samples according to another embodiment of the present invention.
Figure 9:
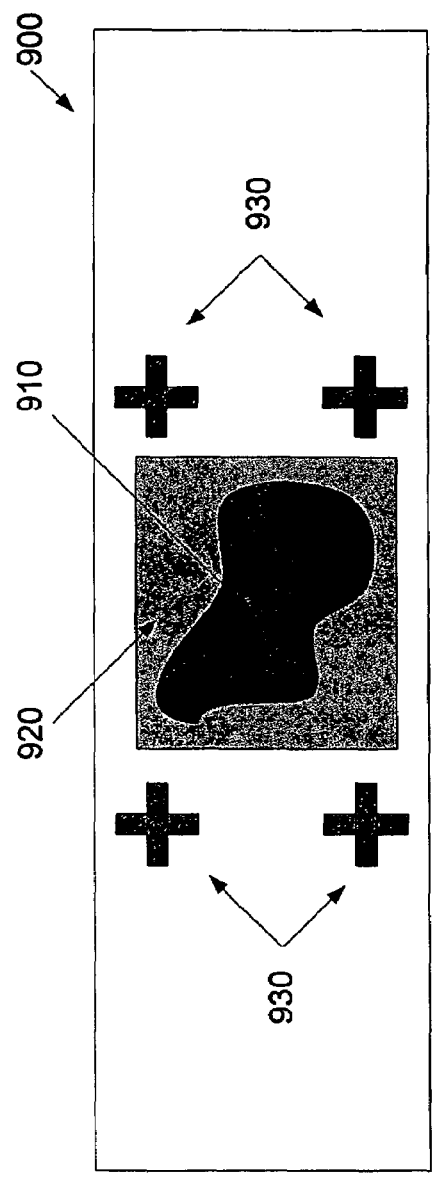
FIG. 9 is an illustration of a slide having alignment marks used for registration according to one embodiment of the present invention.

Referring to FIG. 7, the imaging system according to the present invention can be operated with multiple samples $700_1$, $700_2$, ... $700_n$. Illumination line 760 is provided and samples $700_1$, $700_2$, ... $700_n$ are moved relative to illumination line 760. In the embodiment of FIG. 7, the continuous sample moving technique provides scanning in one direction. In the embodiment of FIG. 8, the continuous sample moving technique provides scanning in both directions. Any number of specimen could be imaged using the arrangements shown in FIGS. 7 and 8.

FIG. 8 depicts an exemplary embodiment of the present invention as applied to batch slide tissue imaging. Samples 800, 805, 810, 820 and 825 are provided on slides (not shown) and each has a size of 15×15 mm. The illumination line may have a length of 0.7 mm. For this example, there are 50 slides in a batch. More or fewer slides may be provided. The magnification is 40×, and the scanning speed is 200 mm/second. The detector is a fast CCD/CMOS camera. The sample support length is 1000 mm.

Similar to the example of FIG. 6, the number of passes per slide is 22. However, the total scan length is 22000 mm. The ideal scan time is 110 s/batch. Correction for additional delays for sample support acceleration, deceleration, sample support shift between lines, etc, is 50% of the ideal scan time. This is smaller than for single slide scanning. The corrected batch scan time is 165 seconds. The average scan time is 3 seconds per slide.

In order to assist in registering samples on slides, at least one alignment mark may be provided on the substrate of the slides. For example, referring to FIG. 9, slide 900 is provided with sample 910 and cover slip 920. A plurality of alignment marks 930 are provided in slide 900. Alignment marks 930 may be formed by scribing or etching the surface of slide 900 or cover slip 920. Although crosses are depicted as alignment marks in FIG. 9, it should be recognized that other shapes, types, number, and location of alignment marks may be used as necessary and desired.

Registration of a sample can be performed in a variety of ways. In one embodiment, registration can be performed prior to the high resolution imaging. In another embodiment, registration can be performed at the same time as the high resolution imaging.

In one embodiment, the excitation light is directed to sample 910 and illuminates alignment marks 930. Successively, the light can be partially absorbed, scattered, reflected or most generally, emitted with a different characteristics, such as a longer wavelength, a modified intensity, etc. The emitted light differs detectably from the background and therefore, an image of the alignment mark can be registered by detector 190 (shown in FIG. 1) or by a separate detector (not shown). This image is registered with each fluorescent channel and can be used, exemplary, during image analysis in a way allowing selecting an area of interest from the tissue sample image.

As depicted in FIG. 10, several methods of registration can be used during imaging based on a characteristic of the emitted light. For example, in one embodiment, the edges of alignment marks may be detected when the excitation light is scattered on the edges, producing characteristic double spike signal in the image space. Such an embodiment is provided in FIG. 10a. In another embodiment, a "W-shaped" signal can be formed due to the reflectivity change on the mark, shown in FIG. 10b. In another embodiment, if the alignment mark was delineated on the substrate in a form of a Fresnel zone target, a single spike signal will be formed due to diffraction on the target. This is illustrated in FIG. 10c. In still another embodiment, a fluorescent signal will be formed if a luminophore material was incorporated into the alignment mark or exemplary, due to a fluorescence behavior of the scribed or etched mark. Such is shown in FIG. 10d.

In one embodiment, reflected light is detected from the alignment marks as well as from the edges of the cover slip. In one embodiment, the alignment mark is recorded with the sample image. The detection of the alignment marks may also be used to control the relative movement of the sample and the illumination system.

Other embodiments, uses, and advantages of the present invention will be apparent to those skilled in the art from consideration of the specification and practice of the invention disclosed herein. The specification and examples should be considered exemplary only.

What is claimed is:

1. A system for multimode imaging of a plurality of samples, comprising:
   at least one light source;
   an optical system selected responsive to a mode of operation of the imaging system; and
   a detector capable of selective reading of pixels;
   wherein an image area of a first sample of one of the plurality of samples is scanned in a plurality of directions, wherein an image area of a second sample of one of the plurality of images is scanned in a plurality of directions, wherein an image area of a third sample of one of the plurality of images is scanned in a plurality of directions.

2. The system of claim 1, wherein the mode of operation is wide field mode.

3. The system of claim 1, wherein the mode of operation is selected from the group consisting of fixed line confocal mode and scanning line confocal mode.

4. The system of claim 1, wherein the mode of operation is point confocal mode.

5. The system of claim 1, wherein the mode of operation is through transmission mode.

6. The system of claim 1, wherein the optical system comprises:
   a beam forming element selected in response to the mode of operation for the imaging system, and
   a beam deflecting device that deflects the light on the at least one sample.

7. The system of claim 1, further comprising:
   a sample support for holding the plurality of samples.

8. The system of claim 6, wherein the optical system further comprises:
   a beam collimator that collimates the light, the beam collimator selected from the group consisting of a lens-based collimator and a mirror-based collimator.

9. The system of claim 6, wherein the beam forming element is selected from the group consisting of Powell lenses, cylindrical lenses, diffraction gratings, holographic elements, focusing mirrors, and combinations thereof.

10. The system of claim 6, wherein the beam forming element is selected from the group consisting of conventional lenses having spherical surfaces, conventional lenses having aspherical surfaces, focusing mirrors, and combinations thereof.

11. The system of claim 6, wherein the beam deflecting device comprises:
    a scanning mirror; and
    at least one actuator.

12. The system of claim 11, wherein the scanning mirror is selected from the group consisting of reflective mirrors and dichroic mirrors.

13. The system of claim 1, farther comprising at least one optical filter.

14. The system of claim 1, further comprising an additional aperture having a physical slit.

15. The system of claim 14, wherein the width of the physical slit is adjustable.

16. A method for multimode imaging of a plurality of samples, comprising:
    selecting a mode of operation for the imaging system;
    transmitting light from at least one light source through an optical system selected in response to the mode of operation for the imaging system;
    scanning an image area of a first sample of the plurality of samples in a plurality of directions;
    scanning an image area of a second sample of the plurality of samples in a plurality of directions;
    scanning an image area of a third sample of the plurality of samples in a plurality of directions; and
    selectively reading pixels of each of image areas of the first sample, the second sample and the third sample of the plurality of samples with a detector.

17. The method of claim 16, wherein the mode of operation is wide field mode.

18. The method of claim 16, wherein the mode of operation is selected from the group consisting of fixed line confocal mode and scanning line confocal mode.

19. The method of claim 16, wherein the mode of operation is point confocal mode.

20. The method of claim 16, wherein the mode of operation is through transmission mode.

21. The method of claim 16, wherein transmitting light from at least one light source through an optical system comprises:
    providing a beam forming element based on the selected mode of operation; and
    deflecting the light on the plurality of samples.

22. The method of claim 21, wherein the beam forming element is selected from the group consisting of Powell lenses, cylindrical lenses, diffraction gratings, holographic elements, focusing mirrors, and combinations thereof.

23. The method of claim 21, wherein the beam forming element is selected from the group consisting of conventional lenses having spherical surfaces, conventional lenses having aspherical surfaces, focusing mirrors, and combinations thereof.

24. The method of claim 21, wherein deflecting the light on the plurality of samples comprises:
    deflecting the light on the at least one sample with a scanning mirror and at least one actuator.

25. The method of claim 16, wherein transmitting light from at least one light source through an optical system comprises:
    collimating the light with a beam collimator selected from the group consisting of a lens-based collimator and a mirror-based collimator.

26. The method of claim 16, further comprising:
    filtering light from the at least one sample with at least one optical filter.

27. The method of claim 16, wherein the plurality of samples are provided on a sample support.

28. A system for multimode imaging a plurality of samples, comprising:
    at least one light source;

an optical system selected responsive to a mode of operation of the imaging system, the mode of operation is selected from the group consisting of wide field mode, fixed line confocal mode, scanning line confocal mode, point confocal mode, and through transmission mode; and a detector capable of selective reading of pixels;

wherein an image area of a first sample of one of the plurality of samples is scanned, wherein an image area of a second sample of one of the plurality of images is scanned, wherein an image area of a third sample of one of the plurality of images is scanned in a plurality of directions relative to the optical system.

29. The system of claim 28, wherein the first, second or third sample of the plurality of samples is moved in the plurality of directions by a step sample movement technique.

* * * * *